United States Patent [19]

Wilbanks

[11] Patent Number: 4,928,360
[45] Date of Patent: May 29, 1990

[54] BOARD ANCHOR

[76] Inventor: John W. Wilbanks, 6806 Log Hollow, #210, Houston, Tex. 77088

[21] Appl. No.: 377,145

[22] Filed: Jul. 10, 1989

[51] Int. Cl.$^5$ ............................................. A44B 13/02
[52] U.S. Cl. ...................................... 24/235; 24/236; 5/82 R
[58] Field of Search ................. 24/235, 236, 237, 599, 24/193; 128/870, 876; 16/252, 262, 263, 264; 5/82 R

[56] References Cited

U.S. PATENT DOCUMENTS

| 380,997 | 4/1888 | Crippen et al. | 24/236 |
| 589,034 | 8/1897 | Schellhammer | 24/235 |
| 847,963 | 3/1907 | Milhollin | 16/262 |
| 3,358,340 | 12/1967 | Higuchi | 24/235 |
| 3,831,229 | 8/1974 | Craven | 24/235 |
| 4,074,401 | 2/1978 | Spinosa et al. | 24/236 |
| 4,158,907 | 6/1979 | Spinosa et al. | 24/236 |
| 4,358,871 | 11/1982 | Takai | 16/262 |
| 4,369,982 | 1/1983 | Hein et al. | 5/82 R |

Primary Examiner—Victor N. Sakran
Attorney, Agent, or Firm—Robert W. B. Dickerson

[57] ABSTRACT

An anchor device for securing a person to a spine board, the anchor being autoclavable and including a hook portion and a yieldable, spring-biased, barrier member for permitting engagement with a board aperture.

6 Claims, 2 Drawing Sheets

4,928,360

BOARD ANCHOR

BACKGROUND OF THE INVENTION

Spine boards have long been used to transfer injured or otherwise incapacitated persons. One such board is illustrated by U.S. Pat. No. 4,369,982, and includes a number of slots, or apertures, spaced along opposite sides thereof. Straps have been used to secure a patient thereto. The mentioned U.S. Pat. No. '982, hooks one end of the straps to a pin transversely disposed across an associated slot. The other end of each pair of oppositely disposed straps would be secured together in the fashion of automotive seat belts. Various other attachment devices are shown in U.S. Pat. Nos. 1,624,561; 2,675,564; 2,896,288; 3,074,136; 3,194,602; 3,358,340; 4,074,401; and 4,158,907. It has always been desirable to be able to quickly and safely remove such straps and associated anchoring means for the board. Likewise it has been necessary for the straps, once anchored, to permit safe transportation of the individual. It has further become extremely desirable to be able to render the anchor sanitary, in spite of any potentially toxic material, including contaminated blood, that may have been in contact therewith. Applicant's anchor has attacked and solved each of these problem areas.

SUMMARY OF THE INVENTION

Patient-securing straps are secured by anchoring means to a number of oppositely positioned apertures spaced along opposed sides of a spine board. Such anchoring means includes a hook-like body, entry into which is removably blocked by a coil-spring biased gate. Said gate and body are secured to a retainer, which, in turn, is removably linked to one end of one of said straps. The anchor is constructed of autoclavable materials.

DESCRIPTION OF A PREFERRED EMBODIMENT

Figure 3:
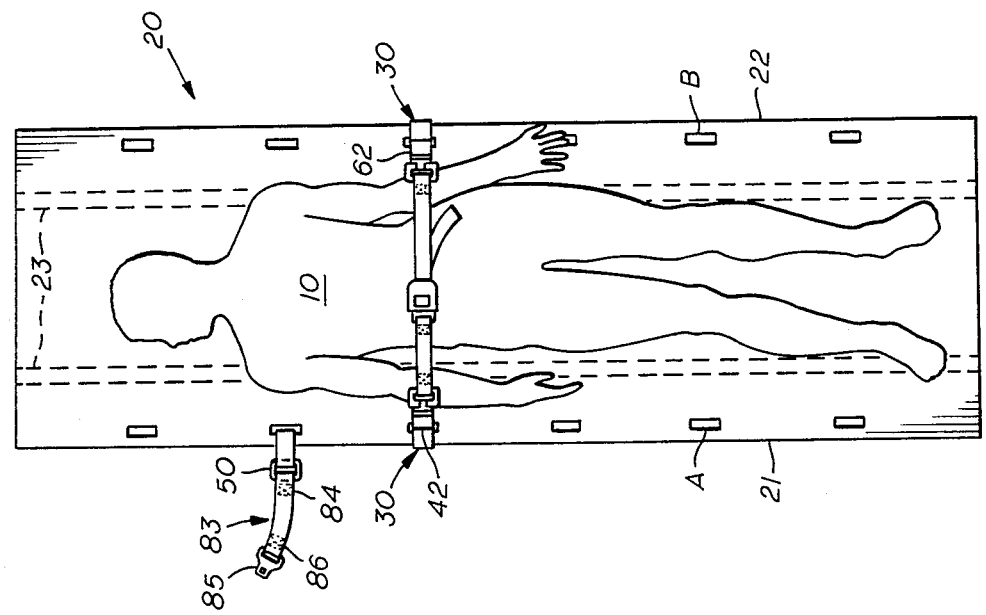
FIG. 3 is a front elevation of a spine board having a plurality of anchor assemblies securing a patient to the board.

An individual 10 is illustrated as being secured to spine board 20. Such board is of a general type common to fire, rescue, EMS, and hospital systems. The board is generally rectangular in configuration, with a series of spaced slots, or apertures, A and B, along opposite sides 21 and 22 of the board. Each of this inventor's anchors would be secured to one of said slots. A pair of longitudinal skids, or runners 23, may extend longitudinally the length of the rear surface of board 20.

The anchor 30 of the invention comprises three principal components, namely body 40, retainer 50, and gate 60. At this point, it should be understood that all anchor components should be fabricated of a material capable of withstanding autoclaving. A preferred material is '304 stainless steel. This is important to safely permit reusing the anchor in spite of toxic, including blood, contamination.

Anchor body 40, is essentially "J" or hook shaped, and includes hook portion 41 having a leading edge 42, and an extended leg 43 having a trailing edge 44. Said hook and leg are joined by, preferably curved, web 45. A pair of spaced apertures 46 extend through leg 43, near its trailing edge.

Retainer 50 is essentially rectangular in configuration with a central rectangular cutout 51, and has upper and lower strut portions 52, 53. Said lower portion is centrally gapped, leaving stubs 53-A and 53-B. Each such stub includes an aperture 56 passing therethrough.

Gate member 60 includes a pair of generally rectangular jaws 61 and 62. Jaw 62 includes leading edge 63, while jaw 61 includes trailing edge 64. Near said trailing edge 64, spaced apertures 66 pass through jaw 61. Along their adjacent edges, said jaws each includes a pair of rolled, or otherwise formed, pin-accommodating tubes. Tubes 65 of jaw 61 are adjacent opposed sides 67-A and 67-B, leaving a substantial gap 68 therebetween. Tubes 69 of a jaw 62 are each spaced laterally inwardly of opposed sides 71-A and 71-B of said jaw 62, and also leave a gap 72 therebetween. Tubes 69 fit within gap 68 so that the passageway through all four tubes 65, 69 may be aligned so as to receive pivot pin 73. Within gap 72, a coiled spring 74 surrounds said pivot pin. One spring end 74-A is seated against jaw 61, and the other spring end 74-B is seated against jaw 62. With jaw 61 secured, as subsequently described, the spring biases jaw 62 in the Direction of arrow 80.

Consider now the assembling of the anchor. A sandwich is formed comprising jaw 61 of gate 60 in the center thereof with leg 43 of body 40 and retainer 50 on opposite sides thereof Retainer cutout 51 is adapted to receive one end 84 of webbing 83. Each of the three pairs of apertures 46, 56, and 66 is aligned, one with the others. Screws 81, preferably of the Allen variety, pass through such apertures to secure the members together. Apertures 46 may each threadedly receive a threaded shank of screws 81, or nuts, or the like (not shown), to secure the components together.

Figure 1:
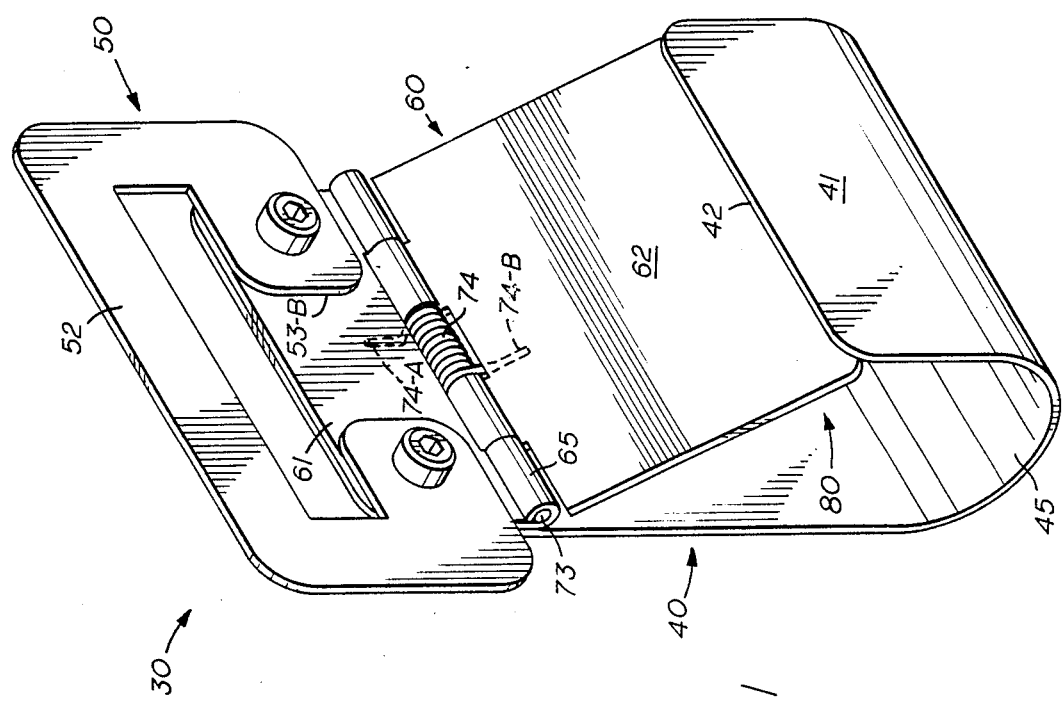
FIG. 1 is a perspective of an assembled anchor.
Figure 2:
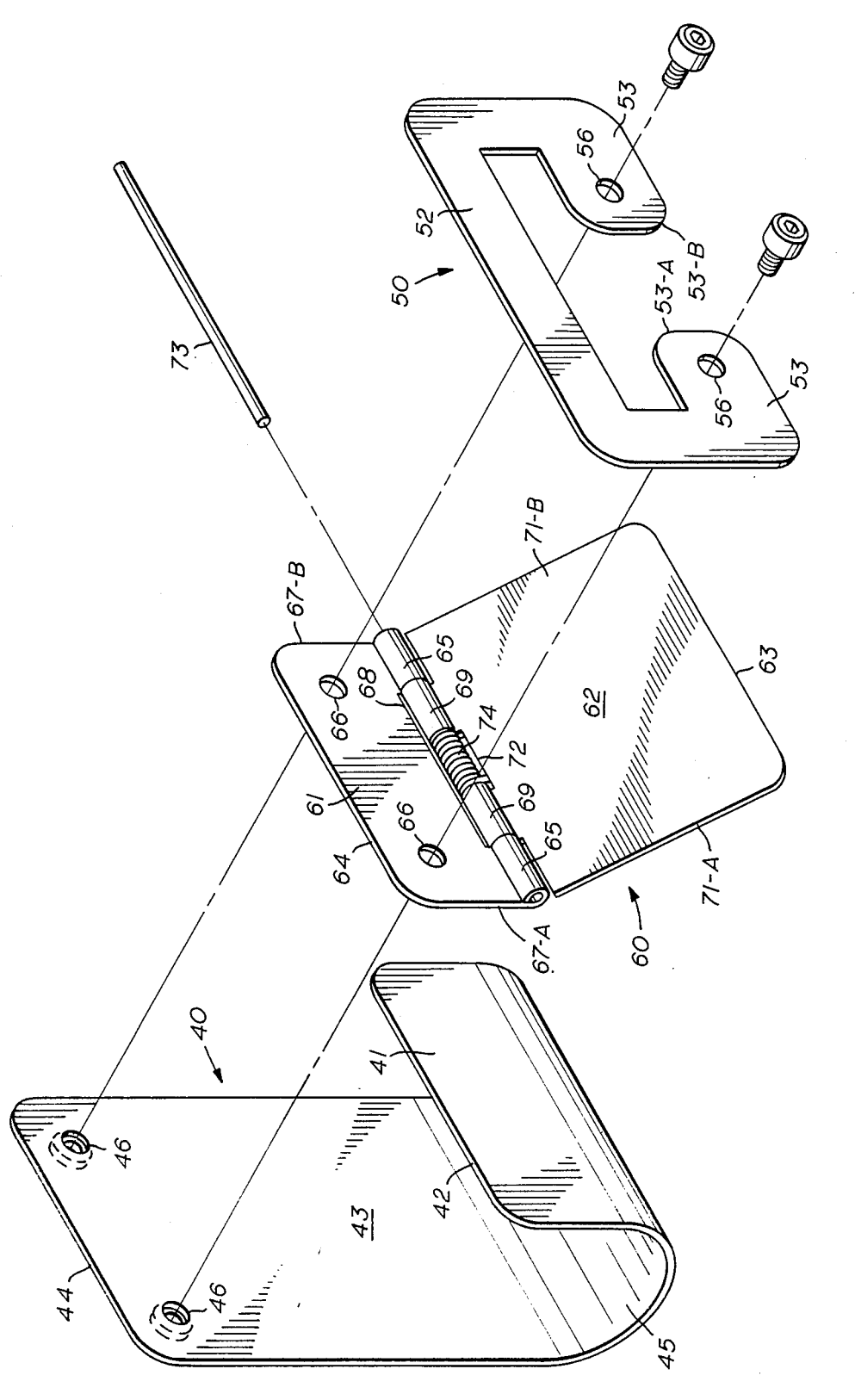
FIG. 2 is an exploded perspective of the anchor of claim 1.

Hook 41 of each anchor would pass through a spine board aperture A or B, forcing gate jaw 62 in the opposite direction to arrow 80. When leading edge 42 sufficiently passes through its respective board aperture A or B, gate jaw 62 will close on hook 41, urged by spring 74. The relatively smooth, reverse side (opposite from FIG. 1), would abut the patient. One anchor would be secured to one of an opposed pair of board apertures. To form an anchor assembly, each anchor would have said one end 84 of a section of webbing, or belting 83 secured to retainer 50, via cutout 51. The securing means, preferably readily removable, may be stitching, snaps or any such means. Thus, the anchor may be field stripped by removing one or more of fasteners 81, permitting the retainer to be removed or pivoted about such a fastener, and removing the webbing. The remaining anchor components may be autoclaved, a section of sterile webbing positioned in slot 51, and the anchor reassembled. A fastener, 85 would be secured to the opposite end 86 of each webbing 83. Obviously, for a related pair of anchor assemblies, one would have a male and the other a female fastener. In fact the "snap assembly" of the previously mentioned Spinosa et al patents '401 and '907, basically comprise such male and female cooperating fasteners, whereas applicant's anchor is generally universal. Such fasteners 85 may normally be adjustable on the webbing to accommodate differently sized loads.

. Inasmuch as the webbing may be readily removed from and replaced on the anchor of this invention, and since the anchor is autoclavable, the device provides a near ultimate in infection control. Further, the anchor may be field serviced, requiring only an Allen wrench for assembly and dissassembly.

Although only a single embodiment has been described, it should be obvious that numerous modifications would be possible by one skilled in the act without departing from the spirit of the invention, the scope of which is limited only by the following claims.

I claim:

1. A spine board anchor comprising:

A body portion having a hook-like portion with a leading edge adapted to pass through a board aperture and an adjacent leg extending laterally from said hook-like portion, said leg having a trailing edge and a pair of spaced apertures through said leg adjacent said trailing edge;

a bifurcated gate, said gate including a pair of spaced jaws linked by pivot means and coiled spring means biasing one of said jaws toward a position blocking removal of said board anchor from said board, the other of said jaws including a pair of spaced apertures therethrough, each of said jaws including pivot-pin-accommodating tube means, pivot pin means insertable through said tube means, said spring means encircling said pivot pin and adapted to regulate movement of said one jaw relative to the other jaw;

a retainer member having a central slot therethrough adapted to receive a section of webbing, said retainer also having a pair of apertures therethrough; and said body portion, gate and retainer are each fabricated of materials rendering them autoclavable and each of their respective pairs of apertures are aligned and removably secured together, sandwich style, by removable fastener means, said sandwich comprising a central member formed by said gate's other jaw and outer members formed respectively by said body portion's adjacent leg and said retainer member, said retainer's slot, stubs and said removable fasteners comprising means permitting ready field disassembly and assembly of said anchor.

2. A spine board anchor assembly comprising:

a pair of anchors each of which includes;

a body portion having a hook-like extremity with a leading edge adapted to pass through an aperture in a spine board, said body portion also having a further extremity having a pair of spaced apertures, said extremities being joined by a web, a bifurcated gate carrying a coiled spring, said gate including a pair of spaced jaws linked by pivot means, said coiled spring biasing one of said jaws toward a position-blocking removal of said board anchor from said board, the other of said jaws including a pair of spaced apertures therethrough, each of said jaws including pivot-pin-accommodating tube means, pivot pin means insertable through said tube means, said spring encircling said pivot pin means and adapted to regulate movement of said one jaw relative to the other jaw, and a retainer member having a central slot therethrough, adapted to receive a section of webbing, said retainer also having a pair of spaced apertures therethrough, said body portion, gate and retainer are each fabricated of materials rending them autoclavable, and each of their respective pairs of apertures are aligned and secured together, sandwich style, by removable fastener means, said sandwich comprising a central member formed by said gate's other jaw and outer members formed respectively by said body portion's adjacent leg and said retainer member, a section of webbing removably joined at one end to said retainer slot, means permitting ready field replacement of said webbing on said retainer slot, and further fastener means for securing together the other end of two adjacent anchor's webbing sections.

3. The assembly of claim 6 wherein said gate includes a pair of jaws, each said jaw including a pair of pin-receiving tubes, one of said jaws having a pair of spaced apertures, said gate further including a pivot pin received by said jaws' tubes, and said coil spring circumscribing at least part of said pin and biasing the other of said jaws toward engagement with said body portion's hook.

4. The assembly of claim 3 and including fastener means releasably securing together said retainer, body and gate, via their respective pairs of apertures.

5. The assembly of claim 4 wherein the material comprising said anchor is autoclavable.

6. The assembly of claim 5 and including a strip of belting means, one end of which is removably secured to said retainer through its central passageway, the other end of said belting carrying one of a male or female fastener.

* * * * *